US00PP23591P3

(12) United States Plant Patent
Egger

(10) Patent No.: US PP23,591 P3
(45) Date of Patent: May 7, 2013

(54) ***TIARELLA* PLANT NAMED 'PACIFIC CREST'**

(50) Latin Name: ***Tiarella* spp.**
Varietal Denomination: Pacific Crest

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 95 days.

(21) Appl. No.: 13/200,485

(22) Filed: Sep. 22, 2011

(65) Prior Publication Data

US 2013/0081188 P1 Mar. 28, 2013

(51) Int. Cl.
*A01H 5/00* (2006.01)

(52) U.S. Cl.
USPC ..... Plt./486

(58) Field of Classification Search ..... Plt./486
See application file for complete search history.

*Primary Examiner* — Susan McCormick Ewoldt
(74) *Attorney, Agent, or Firm* — Klarquist Sparkman, LLP

(57) ABSTRACT

A new and distinct cultivar of *Tiarella* plant characterized by glossy leaves, large, palmately-lobed leaves with the terminal lobe the longest, an excellent trailing habit, dark brown markings following the veins filling up to ¾ of the leaf, and excellent vigor.

1 Drawing Sheet

Botanical denomination: *Tiarella* spp.
Variety designation: 'Pacific Crest'.

BACKGROUND OF THE INVENTION

The present invention relates to a new and distinct cultivar of a hardy herbaceous perennial of the genus *Tiarella*, and known by the cultivar name 'Pacific Crest'. The genus *Tiarella* is a member of the family Saxifragaceae.

The new cultivar originated from a planned breeding program as a cross between *Tiarella* 29-04 as the seed parent and *Tiarella* 29-02, as the pollen parent. Both parents are proprietary, unreleased *Tiarella*.

Compared to *Tiarella* 'Oregon Trail' (U.S. Plant Pat. No. 22,712), the new cultivar has leaves that are larger, glossy, flatter, with the lobes narrower, and with a greater area of red brown in the leaf center.

SUMMARY OF THE INVENTION

This plant is uniquely characterized by the following:

1. glossy leaves,
2. large, palmately-lobed leaves, with the terminal lobe the longest,
3. an excellent trailing habit,
4. dark brown markings following the veins filling up to ¾ of the leaf,
5. and excellent vigor.

The new variety has been reproduced only by asexual propagation (cuttings and micropropagation). Each of the progeny exhibits identical characteristics to the original plant. Asexual propagation by cuttings and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows *Tiarella* 'Pacific Crest' grown outside in the trial bed in May in Canby, Oreg.

FIG. 2 shows a close up of the foliage and flowers in April from plants grown indoors.

DETAILED PLANT DESCRIPTION

The following is a detailed description of the new *Tiarella* cultivar based on observations of 6-month-old plants grown in one gallon containers in a warm greenhouse in April in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart, 5$^{th}$ edition.

Plant:

*Type*.—Herbaceous perennial.
*Hardiness*.—USDA Zones 4 to 9.
*Form*.—Trailing.
*Size*.—55 cm wide and 15 cm high from the soil to the top of the foliage.
*Vigor*.—Excellent.
*Roots*.—Fibrous, freely branching, fine, and white in color; roots develop easily from stem cuttings.

Stem:

*Type*.—Decumbent with adventitious roots at the nodes.
*Size*.—Grows to 3 mm wide and 30 cm long.
*Surface*.—Pubescent.
*Internodes*.—2 cm to 3 cm long.
*Color*.—Between Brown 200B and Greyed Purple 187B.

Basal leaves:

*Type*.—Simple.
*Arrangement*.—Rosette.

*Shape*.—Ovate overall.
*Lobing*.—Variable and deeply cut, 7 main lobes, terminal lobe the longest, all with secondary lobes.
*Margins*.—Irregularly deeply crenate.
*Venation*.—Palmate.
*Apex*.—Acute.
*Base*.—Cordate, overlapping.
*Blade*.—Grows to 9.5 cm long and 9 cm wide.
*Surface*.—Hispid top and bottom, glossy.
*Petiole description*.—10 to 16 cm long and 2.5 mm wide, hirsute, Grey Brown N199B.
*Leaf color*.—Topside, Green 137A with the leaf center pattern Greyed Purple N187A; bottom side Yellow Green 147B with markings tinted Greyed Purple N187A.

Stem leaves:
*Type*.—Simple.
*Arrangement*.—Alternate.
*Shape*.—Ovate overall.
*Lobing*.—Variable, 7 lobes, deeply cut with open sinuses, the terminal lobe the longest, each lobe with secondary lobes.
*Margins*.—Serrate and lobed.
*Venation*.—Palmate.
*Apex*.—Mucronulate.
*Base*.—Cordate, overlapping.
*Blade*.—Grows to 11 cm long and 10.5 cm wide.
*Surface*.—Hispid top and bottom, glossy.
*Petiole description*.—7 to 9 cm long and 2 mm wide, hirsute, between Brown 200B and Greyed Purple 187B.
*Leaf color*.—Topside, Green 137A with the leaf center pattern Greyed Purple N187A; bottom side Yellow Green 147B with markings tinted Greyed Purple N187A.

Inflorescence:
*Type*.—Raceme.
*Flower number*.—About 30 per raceme.
*Size of inflorescences*.—Grows to 17 cm long and 3 cm wide.
*Number of inflorescences*.—20 in first spring flush.
*Bloom period*.—March to mid June in Canby, Oreg.
*Peduncle*.—Unbranched to once branched, grows to 18 cm long and 2.5 mm wide at the base, hispid, between Brown 200B and Greyed Purple 187B.
*Pedicel*.—5 mm long and 1 mm wide, hispid, White N155B.
*Lastingness*.—A raceme blooms for about 3 weeks.

Flower bud:
*Size*.—5 mm deep and 3 mm wide.
*Description*.—Ovoid, down facing until open.
*Surface*.—Glandular.
*Color*.—Light pink, White N155B.

Flower:
*Type*.—Perfect, actinomorphic, sepals petaloid.
*Shape*.—Rotate.
*Flower size*.—8 mm wide and 6 mm deep including stamens and pistil.
*Corolla*.—5 petals, each 4 mm long and 1 mm wide, lanceolate with a clawed base, margin entire, tip acuminate, glabrous on both sides, White NN155D inside and outside.
*Calyx*.—5 mm wide and 2 mm deep, 5 sepals, backs glandular, inside glabrous, petaloid, parted almost to the base; lobes obovate, tips obtuse, margins entire, 2.5 mm long and 1.5 mm wide, White NN155C.
*Stamens*.—10, conspicuously exerted; filaments 5 mm long, White NN155D; anthers undehisced Red 37B; pollen Yellow Orange 22A.
*Pistil*.—1, White N155B, 5 mm long and 2 mm wide, ovary 2 mm long and 2 mm wide, glandular.
*Fragrance*.—None.

Fruit and seed: 6 mm long and 2.5 mm wide, Yellow Green 146C with little seed set; seed Brown 200A, oval, 1.5 mm long.

Pest and disease resistance: This new hybrid shows good mildew tolerance, the main problem for *Tiarella*. No major pest problems. It is susceptible to root weevils, like all *Tiarella*.

I claim:

1. A new and distinct cultivar of *Tiarella* plant herein illustrated and described.

* * * * *

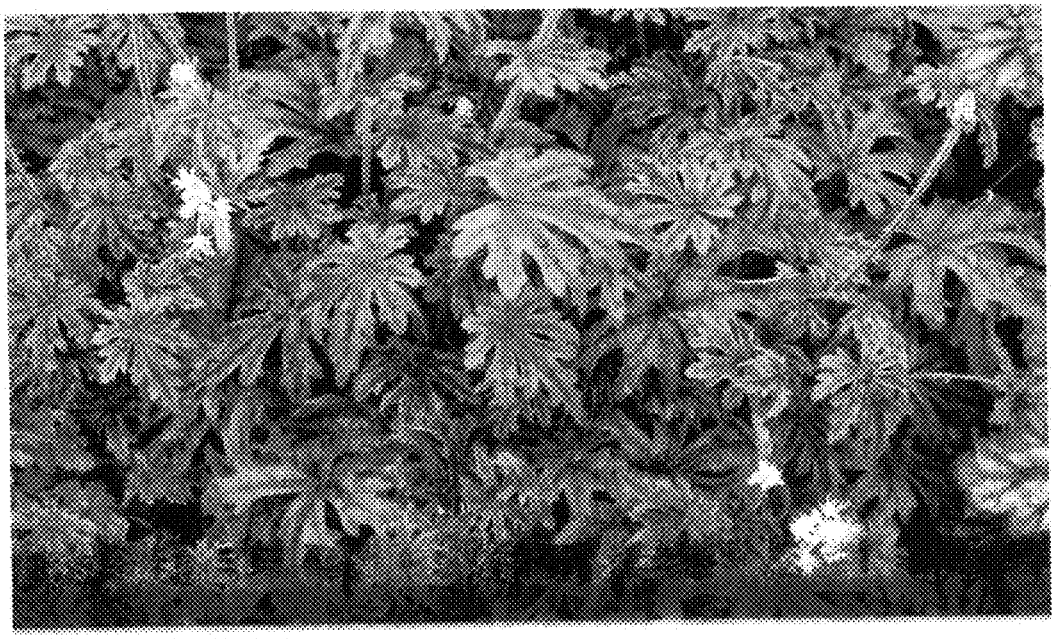

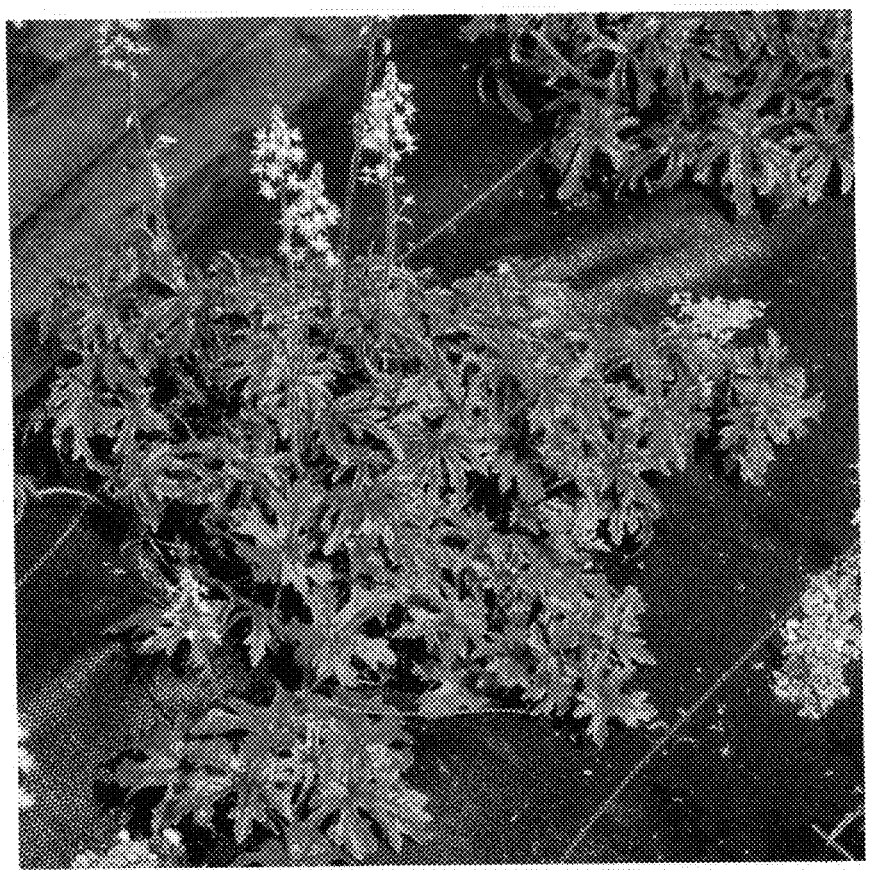
FIG. 1 above, FIG. 2 below